(12) United States Patent
Locke et al.

(10) Patent No.: US 12,343,239 B2
(45) Date of Patent: Jul. 1, 2025

(54) HAND DRESSING FOR USE WITH NEGATIVE PRESSURE WOUND THERAPY

(71) Applicant: Solventum Intellectual Properties Company, Maplewood, MN (US)

(72) Inventors: Christopher Brian Locke, Bournemouth (GB); Thomas Alan Edwards, Hampshire (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 342 days.

(21) Appl. No.: 17/629,233

(22) PCT Filed: Jul. 30, 2020

(86) PCT No.: PCT/IB2020/057197
§ 371 (c)(1),
(2) Date: Jan. 21, 2022

(87) PCT Pub. No.: WO2021/019486
PCT Pub. Date: Feb. 4, 2021

(65) Prior Publication Data
US 2022/0265478 A1 Aug. 25, 2022

Related U.S. Application Data

(60) Provisional application No. 62/881,591, filed on Aug. 1, 2019.

(51) Int. Cl.
A61F 13/05 (2024.01)
A61F 13/10 (2006.01)
A61M 1/00 (2006.01)

(52) U.S. Cl.
CPC ............. *A61F 13/05* (2024.01); *A61F 13/104* (2013.01); *A61M 1/73* (2021.05); *A61M 1/74* (2021.05);
(Continued)

(58) Field of Classification Search
CPC ............ A61F 13/05; A61F 2013/00536; A61F 13/104; A61F 13/10; A61M 1/90;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for corresponding Application No. PCT/IB2020/057197 mailed Oct. 16, 2020.
(Continued)

*Primary Examiner* — Jessica Arble
*Assistant Examiner* — Nhu Q. Tran

(57) ABSTRACT

A dressing includes a barrier film layer, a wound contact layer coupled to the barrier film layer, and a plurality of felted foam strips positioned between the barrier film layer and the wound contact layer. Each strip provides a manifolding pathway. The barrier film layer and the wound contact layer include a central region and a plurality of peninsular projections extending therefrom in the shape of a hand.

10 Claims, 13 Drawing Sheets

(52) U.S. Cl.
CPC .............. *A61M 1/77* (2021.05); *A61M 1/915* (2021.05); *A61M 1/917* (2021.05); *A61M 1/92* (2021.05); *A61M 1/96* (2021.05); *A61M 2205/332* (2013.01); *A61M 2205/3324* (2013.01); *A61M 2205/3344* (2013.01); *A61M 2205/3569* (2013.01); *A61M 2205/50* (2013.01)

(58) Field of Classification Search
CPC .......... A61M 1/77; A61M 1/71; A61M 27/00; A61M 2205/332; A61M 2205/3324; A61M 2205/3344; A61M 2205/3569
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0186260 A1 | 8/2005 | Narini et al. |
| 2007/0000021 A1* | 1/2007 | Yang .................. A41D 19/0006 2/161.6 |
| 2008/0312613 A1* | 12/2008 | Heaton ............. A61F 13/01021 604/313 |
| 2011/0224630 A1* | 9/2011 | Simmons ................ A61F 13/05 604/317 |
| 2013/0198938 A1* | 8/2013 | Birnbaum ............ A41B 11/125 2/311 |
| 2014/0094761 A1* | 4/2014 | Corley .................... A61F 13/05 604/319 |
| 2014/0163491 A1 | 6/2014 | Schuessler et al. |
| 2015/0080788 A1 | 3/2015 | Blott et al. |
| 2015/0320603 A1* | 11/2015 | Locke .................... A61L 31/06 604/543 |
| 2016/0144084 A1* | 5/2016 | Collinson ............... A61F 13/05 604/319 |
| 2017/0007751 A1* | 1/2017 | Hartwell ........... A61F 13/00059 |

(56) References Cited

U.S. PATENT DOCUMENTS

| | | | |
|---|---|---|---|
| 2017/0049943 | A1* | 2/2017 | Balasubramaniam ........................ A61F 13/01029 |
| 2018/0140755 | A1* | 5/2018 | Blott ........................ A61F 13/05 |
| 2018/0353339 | A1 | 12/2018 | Locke et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| DE | 202018005662 U1 | 2/2019 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 1762205 A2 | 3/2007 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2019027731 A1 | 2/2019 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, Ž. Maksimovi?, ?. Radak, and P. Pežka, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

(56) References Cited

OTHER PUBLICATIONS

C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

HAND DRESSING FOR USE WITH NEGATIVE PRESSURE WOUND THERAPY

CROSS-REFERENCE TO RELATED APPLICATIONS

This application claims the benefit of priority to U.S. Provisional Application No. 62/881,591, filed on Aug. 1, 2019, which is incorporated herein by reference in its entirety.

BACKGROUND

The present invention relates generally to the field of treating wounds (e.g., burns, lacerations, surgical incisions, sores, ulcers, damaged tissue, nerve damage, etc.) and more particularly to negative pressure wound therapy systems with instillation therapy. Negative pressure wound therapy refers to the application of negative pressure (relative to atmospheric pressure) to a wound bed to facilitate healing of the wound bed. Negative pressure may be applied in coordination with instillation therapy, in which instillation fluid (e.g., cleansing fluid, medicated fluid, antibiotic fluid, irrigation fluid) is applied to the wound bed. Negative pressure and instillation wound therapy (NPWTi) may facilitate removal of wound exudate and other debris from the wound bed and otherwise support healing.

One common location for a wound (e.g., a burn) that could benefit from NPWTi is on a patient's hand. However, standard NPWTi dressings may be challenging to use on a hand due to the shape, size, contours, articulation, etc. of a hand. Accordingly, hand-specific dressings may facilitate improved NPWTi for hand wounds.

SUMMARY

One implementation of the present disclosure is a dressing. The dressing includes a barrier film layer, a wound contact layer coupled to the barrier film layer, and a plurality of felted foam strips positioned between the barrier film layer and the wound contact layer. Each strip provides a manifolding pathway. The barrier film layer and the wound contact layer include a central region and a plurality of peninsular projections extending therefrom in the shape of a hand.

In some embodiments, each strip extends from the central region to one of the plurality of peninsular projections. The dressing can include a felted foam pad positioned at the central region, with the plurality of strips extending from the felted foam pad. The felted foam strips may be configured to allow airflow between the peninsular region and the felted foam pad. The dressing can include a connection assembly coupled to the barrier film layer at the felted foam pad. The connection assembly is configured to provide airflow between the felted foam pad and a tube coupled to the connection assembly.

In some embodiments, the barrier film layer and the wound contact layer are configured to form wrinkles therein when air is removed from the dressing via the felted foam strips. The wrinkles can allow fluid to flow therethrough.

In some embodiments, the felted foam strips include an open-cell foam. The wound contact layer and the barrier film layer may be configured to allow visual observation of a wound through the wound contact layer and the barrier film layer.

In some embodiments, the barrier film layer is welded to the wound contact layer around a perimeter of the barrier film layer and at a plurality of spot welds distributed amongst the plurality of felted foam strips. The spot welds constrain movement of the plurality of felted foam strips relative to the barrier film layer and the wound contact layer.

In some embodiments, the barrier film layer, the wound contact layer, and the plurality of felted foam strips are formed as a first side of a glove assembly. The first side of the glove assembly is coupled to a second side of the glove assembly to form the glove assembly. The second side of the glove assembly may include a second barrier film layer, a second wound contact layer coupled to the second barrier film layer, and a plurality of second felted foam strips positioned between the barrier film layer and the wound contact layer. Each strip provides a manifolding pathway. The dressing may include a felted foam cuff fluidly communicable with the plurality of felted foam strips of the first side and the plurality of second felted foam strips of the second side.

In some embodiments, the glove assembly is configured to receive a hand of a patient between the wound contact layer and the second wound contact layer. The dressing may include an adhesive configured to seal the first the first side and the second side to a wrist of the patient when the glove assembly receives the hand. The barrier film layer and the second barrier film layer provide a substantially airtight volume therebetween when the adhesive is sealed to the wrist of the patient.

Another implementation of the present disclosure is a wound therapy system. The wound therapy system includes a pump, a tube coupled to the pump, and a glove-shaped dressing coupled to the tube. The glove shaped dressing includes a barrier film layer, a wound contact layer coupled to the barrier film layer, and a plurality of felted foam strips positioned between the barrier film layer and the wound contact layer. The barrier film layer and the wound contact layer include a central region and a plurality of peninsular projections extending therefrom in the shape of a hand. Each of the plurality of felted foam strips extend from the central region to one of the plurality of peninsular projections.

In some embodiments, the felted foam strips are fluidly communicable with the pump via the tube. The pump is configured to draw a negative pressure at the felted foam strips. The barrier film layer and the wound contact layer may be configured to form wrinkles when the pump draws the negative pressure at the felted foam strips. The wrinkles can allow airflow therethrough. In some embodiments, the barrier film layer and the wound contact layer are configured to allow a wound to be visually observed therethrough.

In some embodiments, the wound therapy system includes a felted foam pad positioned at the central region. The plurality of felted foam strips extend from the felted foam pad and the tube is coupled to the glove-shaped dressing proximate the felted foam pad.

Another implementation of the present disclosure is a method. The method includes inserting a hand of a patient into a glove-shaped dressing. The glove-shaped dressing includes a wound contact layer, a barrier film layer, and a plurality of felted foam strips positioned between the barrier film layer and the wound contact layer. The method also includes sealing the glove-shaped dressing around a wrist of the patient, coupling the glove-shaped dressing to a pump such that the pump is in fluid communication with the plurality of felted foam strips, and operating the pump to remove air from the felted foam strips.

In some embodiments, the method includes forming creases in the barrier film layer by operating the pump to remove air from the glove-shaped dressing via the felted foam strips. Operating the pump may cause fluid to flow through the creases.

In some embodiments, coupling the glove-shaped dressing to the pump comprises positioning a connection pad on the barrier film layer at a felted foam pad. The plurality of felted foam strips extend from the felted foam pad. The method may also include coupling a tube to the pump and the connection pad.

DETAILED DESCRIPTION

Negative Pressure and Instillation Wound Therapy System

Figure 1:
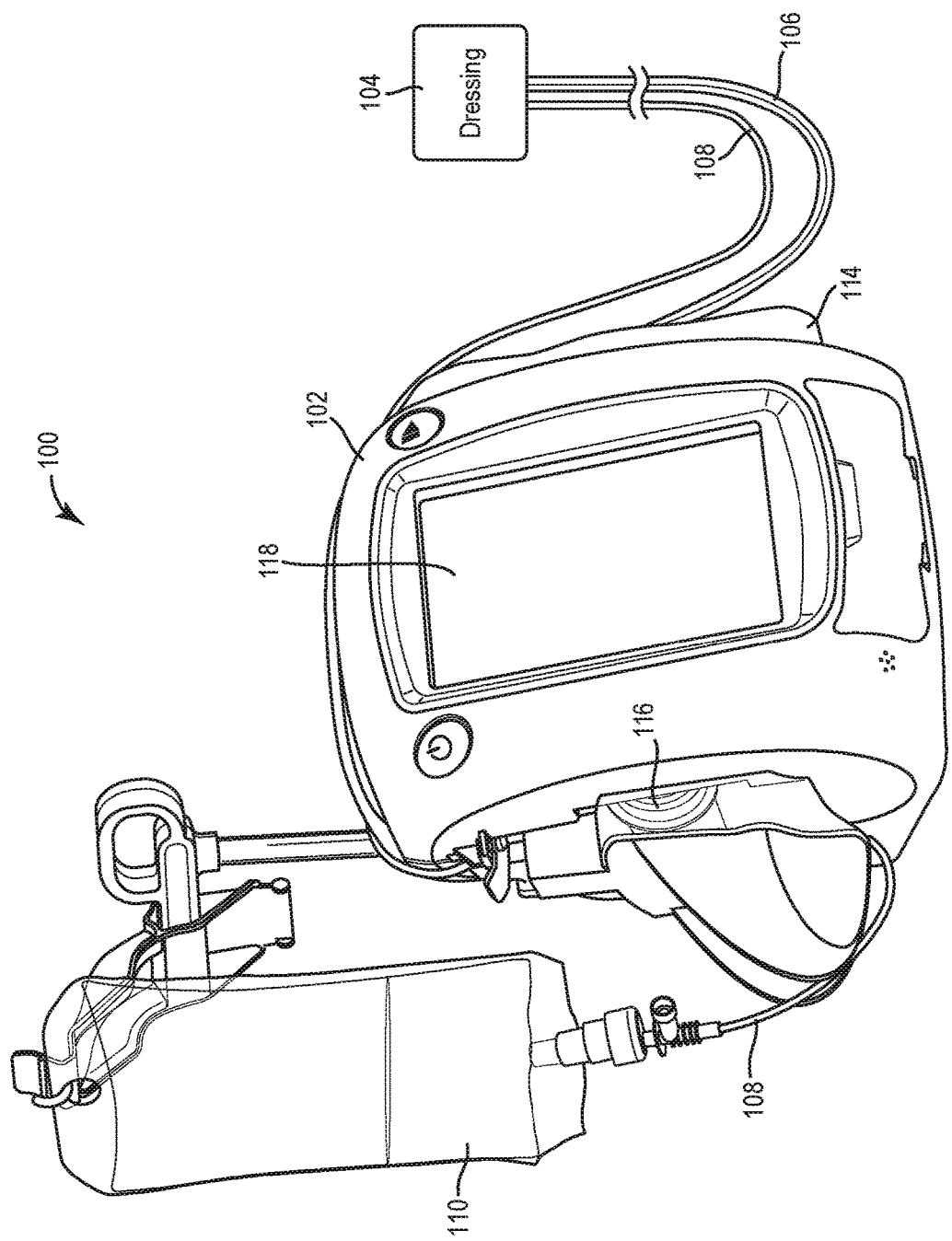
FIG. 1 is a perspective view of a negative pressure and installation wound therapy (NPWTi) system, according to an exemplary embodiment.
Figure 2:
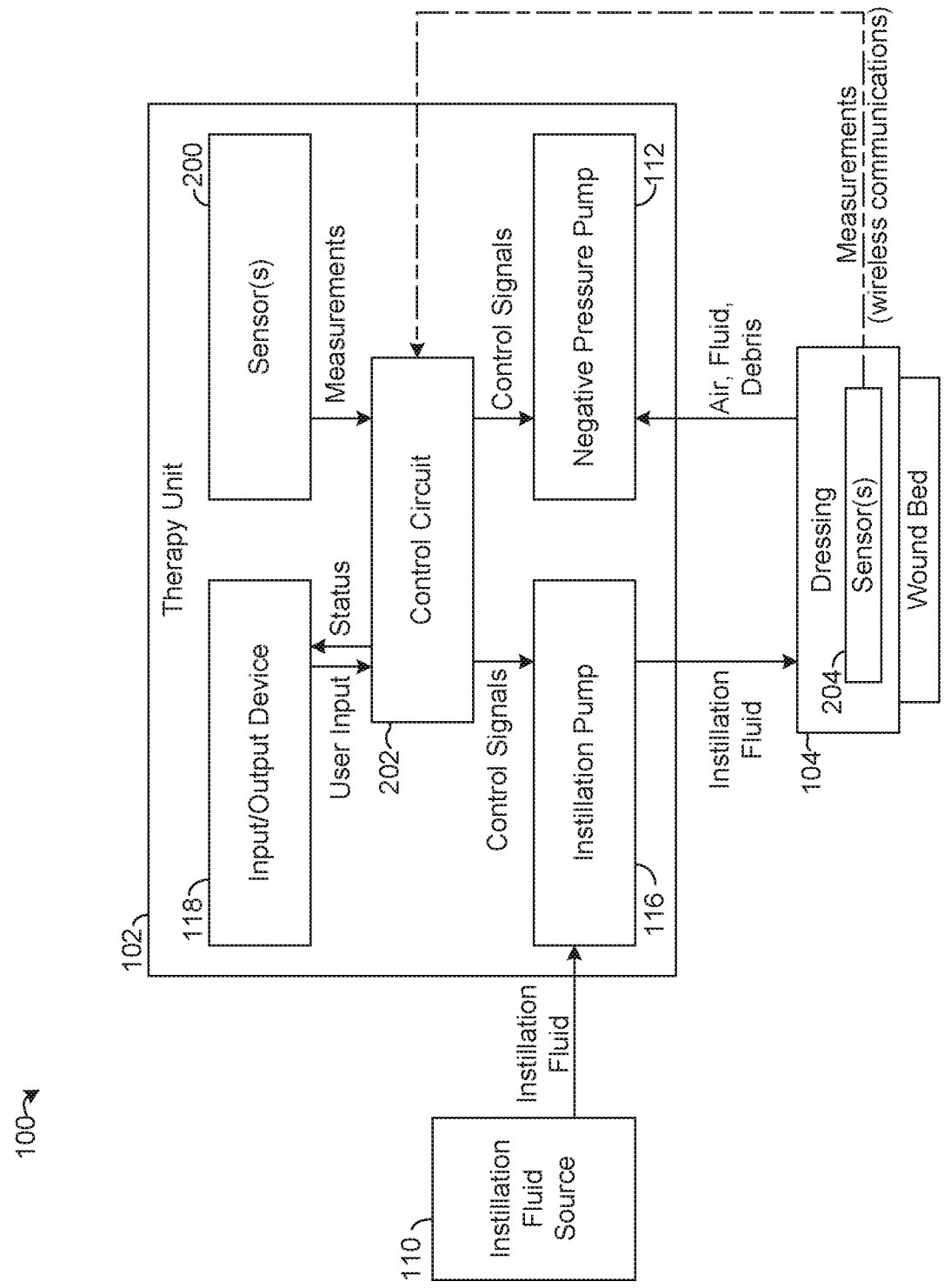
FIG. 2 is a block diagram of the NPWTi system of FIG. 1, according to an exemplary embodiment.

Referring to FIGS. 1 and 2, a negative pressure and instillation wound therapy (NPWTi) system 100 is shown, according to exemplary embodiments. FIG. 1 shows a perspective view of the NPWTi system 100, according to an exemplary embodiment. FIG. 2 shows a block diagram of the NPWTi system 100, according to an exemplary embodiment. The NPWTi system 100 is shown to include a therapy unit 102 fluidly coupled to a dressing 104 via a vacuum tube 106 and an instillation tube 108. In the embodiments described herein, the dressing 104 is configured for use in treating one or more wounds on a patient's hand. The NPWTi system 100 is also shown to include an instillation fluid source 110 fluidly coupled to the instillation tube 108. The NPWTi system 100 is configured to provide negative pressure wound therapy at a wound bed by reducing the pressure at the dressing 104 relative to atmospheric pressure. The NPWTi system 100 is also configured to provide installation therapy by providing instillation fluid to the dressing 104. By providing both negative pressure wound therapy and instillation therapy, the NPWTi system 100 is configured to facilitate wound healing. As described in detail below, the NPWTi system 100 is also configured to provide a physiotherapy mode that facilitates mobility, articulation, etc. of a patient's hand during treatment by the NPWTi system 100. The NPWTi system 100 thereby facilitates wound healing while also allowing for functional rehabilitation of the hand and reducing the risk of contractures.

Although the examples described herein show a NPWTi system 100 configured to provide both negative pressure wound therapy and instillation therapy, in other embodiments the system 100 is configured to provide negative pressure wound therapy (NPWT) without instillation therapy.

The dressing 104 is coupleable to a wound bed, i.e., a location of a wound (e.g., sore, laceration, burn, etc.) on a patient. In the examples herein, the dressing 104 is configured to be placed on a hand of a patient to cover a wound bed located on the hand. The dressing 104 may be substantially sealed over/around the wound bed such that a pressure differential may be maintained between the atmosphere and the wound bed (i.e., across the dressing 104). The dressing 104 may be coupled to the vacuum tube 106 and the instillation tube 108, for example to place the vacuum tube 106 and/or the instillation tube 108 in fluid communication with the wound bed. Embodiments of the dressing 104 are shown in FIGS. 3-9 and described in detail with reference thereto.

The dressing 104 includes one or more sensors 204. The one or more sensor(s) 204 are configured to measure one or more physical parameters at the dressing and provide the measurements to the control circuit 202, for example by transmitting the measurements via wireless communications (e.g., via a wireless network such as Bluetooth, WiFi, etc.). In the embodiments shown herein, the one or more sensor(s) 104 include a humidity sensor configured to measure humidity at the dressing 104, a moisture sensor configured to measure moisture at the dressing 104, and a strain sensor configured to measure a strain on the dressing 104. In some embodiments, the one or more sensor(s) 204 include one or more pH sensors to measure tissue pH or fluid pH.

The therapy unit 102 includes a negative pressure pump 112 (shown in FIG. 2 and obscured within the therapy unit 102 in the perspective view of FIG. 1) configured to pump air, wound exudate, and/or other debris (e.g., necrotic tissue) and/or fluids (e.g., instillation fluid) out of the dressing 104 via the vacuum tube 106, thereby creating a negative pressure at the dressing 104. The negative pressure pump 112 is fluidly communicable with the vacuum tube 106 and the dressing 104. Wound exudate and/or other debris and/or fluids removed from the wound bed by the negative pressure pump 112 may be collected in a canister 114 located on the therapy unit 102. The canister 114 may be removable from the therapy unit 102 to allow canister 114 to be emptied or replaced when the canister 114 fills with fluid and debris.

Operating the negative pressure pump 112 may therefore both create a negative pressure at the wound bed and remove undesirable fluid and debris from the wound bed. In some cases, operating the negative pressure pump 112 may cause deformation of the wound bed and/or provide other energy to the wound bed to facilitate debridement and healing of the wound bed. In various embodiments, the negative pressure pump 112 may be operated to provide various levels (amounts, values, etc.) of negative pressure at the wound bed (e.g., 30 mmHg, 60 mmHg, 75 mmHg, 125 mmHg, 150 mmHg, etc.) for example varying over time as part of a dynamic pressure control approach. In the embodiments described below, the negative pressure pump 112 is configured to operate, as controlled by the control circuit 202, to provide a first level of negative pressure at the wound bed corresponding to a wound therapy mode (e.g., 125 mmHg) and a second level of negative pressure at the wound bed corresponding to a physiotherapy mode (e.g., 60 mmHg), where the second level is closer to ambient air pressure than the first level.

The therapy unit 102 also includes an instillation pump 116. The instillation pump 116 is configured to selectively provide instillation fluid from the instillation fluid source 110 to the dressing 104. The instillation pump 116 is operable to control the timing and amount (volume) of instillation fluid provided to the dressing 104. The instillation pump 116 may be controlled in coordination with the negative pressure pump 112 to provide one or more wound treatment cycles that may facilitate wound healing. In some embodiments, the amount of fluid provided by the instillation pump is automatically determined using a wound volume estimation process executed by the therapy unit 102.

The therapy unit 102 is also shown to include an input/output device 118. The input/output device 118 is configured to provide information relating to the operation of the NPWTi system 100 to a user and to receive user input from the user. The input/output device 118 may display status information relating to the NPWTi system 100, for example including measurements obtained from the sensor(s) 204 of the dressing 104 or the sensor(s) 200 of the therapy unit 102. The input/output device 118 may allow a user to input various preferences, settings, commands, etc. that may be used in controlling the negative pressure pump 112 and the instillation pump 116 as described in detail below. The input/output device 118 may include a display (e.g., a touchscreen), one or more buttons, one or more speakers, and/or various other devices configured to provide information to a user and/or receive input from a user.

As shown in FIG. 2, the therapy unit 102 is also shown to include one or more sensors 200 and a control circuit 202. The sensor(s) 200 may be configured to monitor one or more of various physical parameters relating to the operation of the NPWTi system 100. For example, the sensor(s) 200 may measure pressure at the vacuum tube 106, which may be substantially equivalent and/or otherwise indicative of the pressure at the dressing 104. As another example, the sensor(s) 200 may measure an amount (e.g., volume) of instillation fluid provided to the dressing 104 by the instillation pump 116. The sensor(s) 200 may provide such measurements to the control circuit 202.

The control circuit 202 is configured to control the operation of the therapy unit 102, including by controlling the negative pressure pump 112, the instillation pump 116, and the input/output device 118. The control circuit 202 may receive measurements from the sensor(s) 200 and the sensor(s) 204 and/or user input from the input/output device 118 and use the measurements and/or the user input to generate control signals for the instillation pump 116 and/or the negative pressure pump 112. For example, the control circuit 202 may control the negative pressure pump 112 and the instillation pump 116 to provide various combinations of various instillation phases, soak periods, and negative pressure phases (i.e., various pressures and instillation amounts over various durations) to support and encourage wound healing. As another example, as described in detail below with reference to FIG. 10, the control circuit 202 is configured to automatically initiate a wound therapy mode in response to strain measurements from the sensor(s) 204 by controlling the negative pressure pump 112 to reduce the negative pressure at the dressing 104, thereby allowing increased mobility, flexion, articulation, etc. of the hand treated by the dressing 104.

Hand Dressing for NPWTi or NPWT

Figure 3:
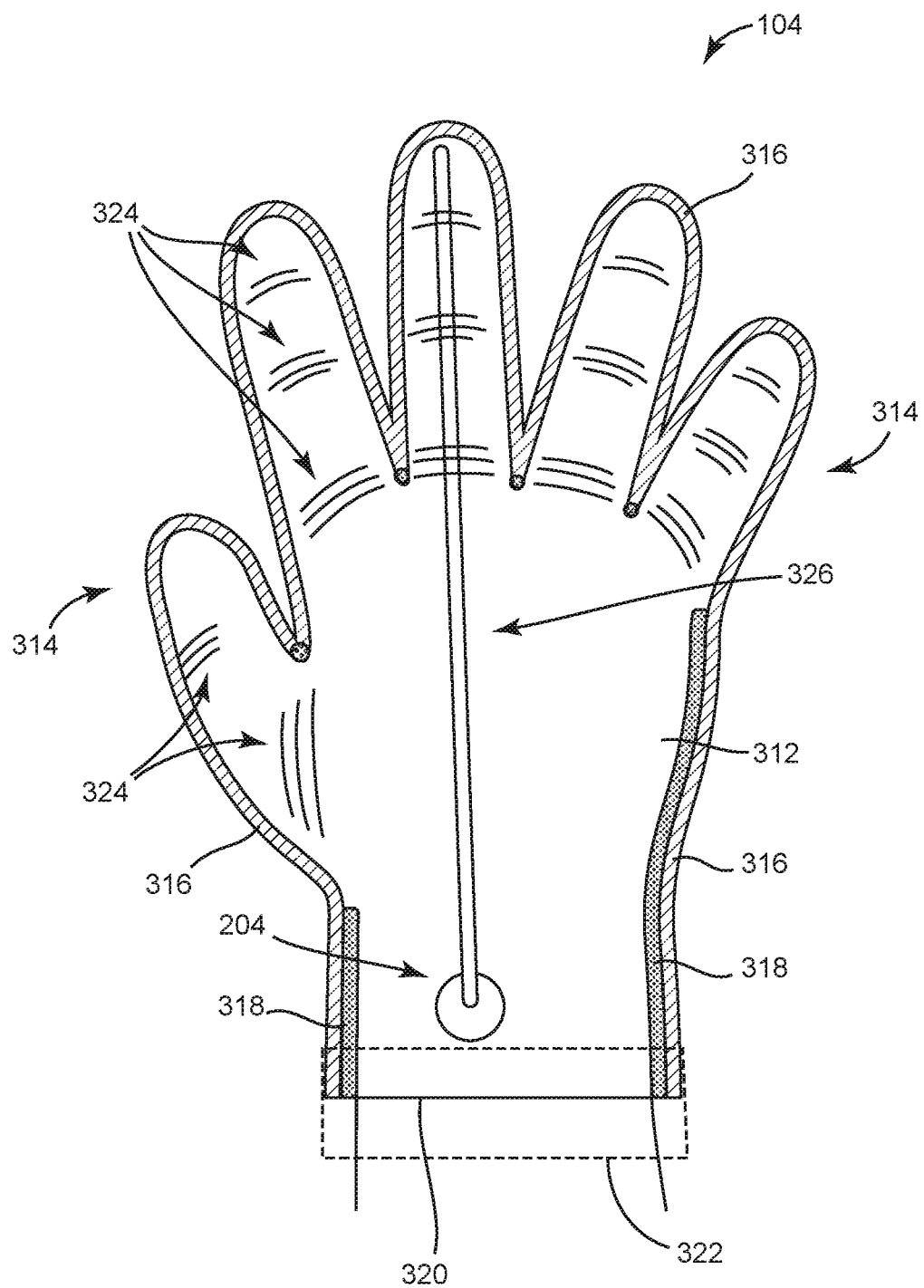
FIG. 3 is a top view of dressing for treating a hand wound and for use with the NPWTi system of FIGS. 1-2, according to an exemplary embodiment.
Figure 4:
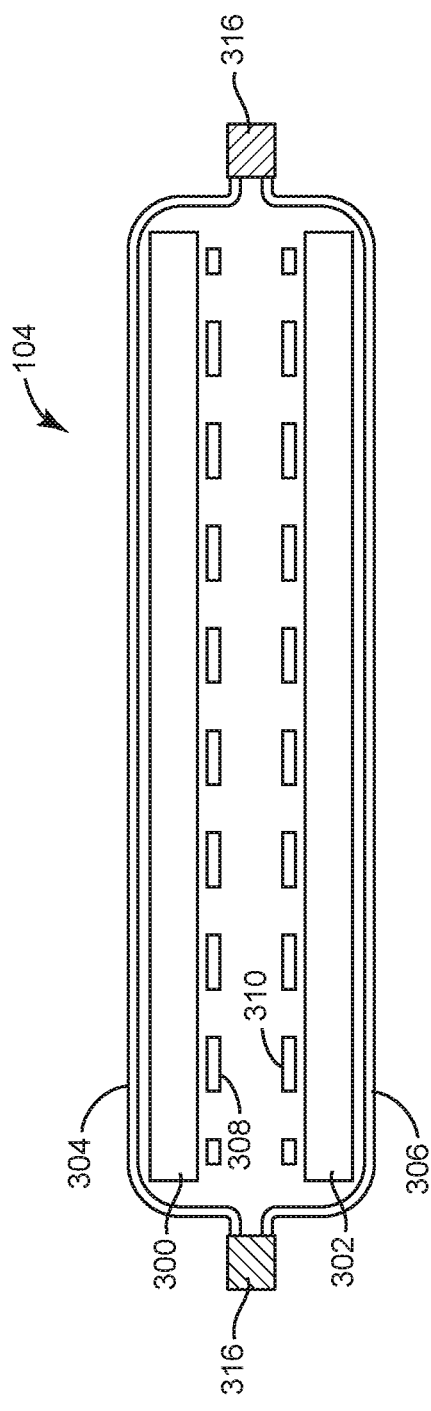
FIG. 4 is a first cross-section view of the dressing of FIG. 3, according to an exemplary embodiment.
Figure 5:
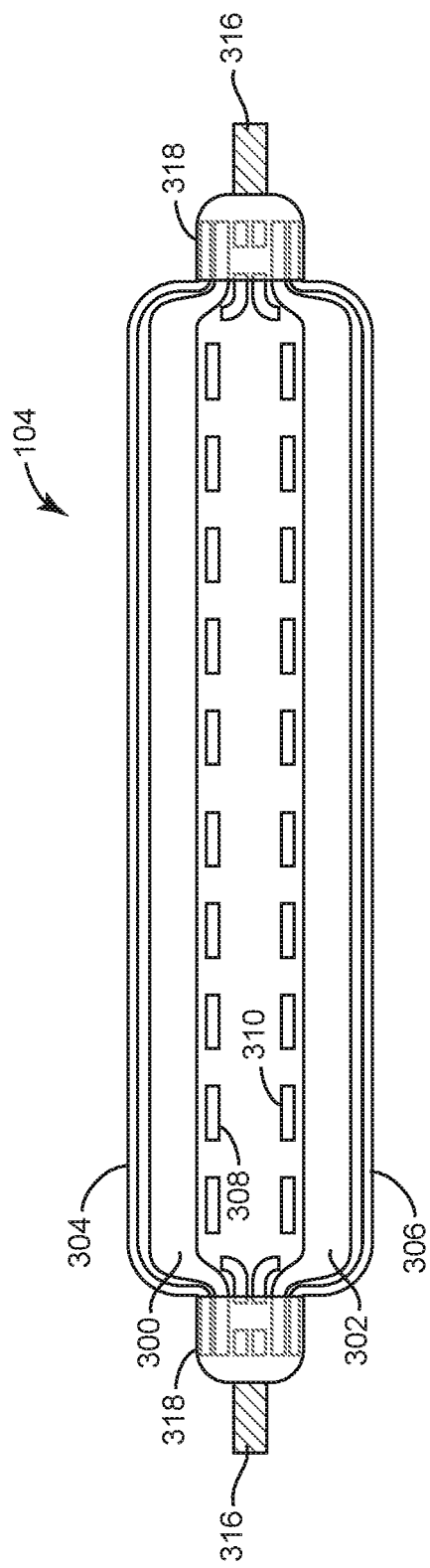
FIG. 5 is a second cross-section view of the dressing of FIG. 3, according to an exemplary embodiment.
Figure 6:
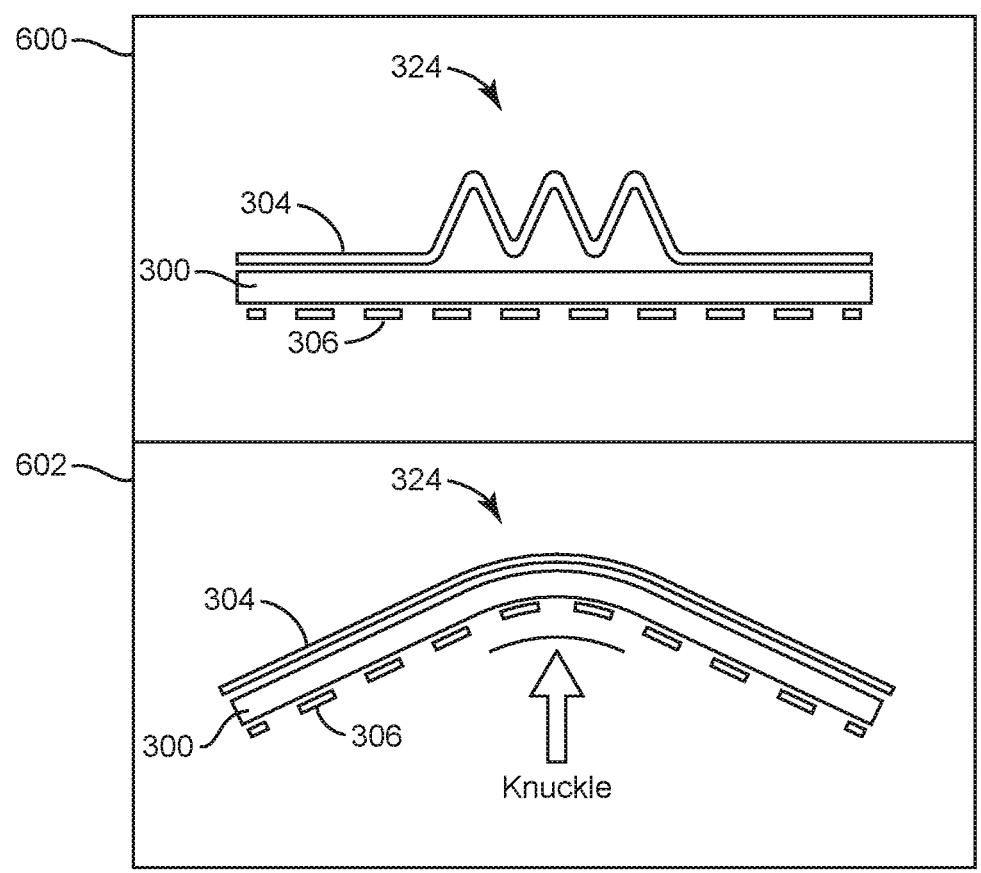
FIG. 6 is a third cross-section view of the dressing of FIG. 3, according to an exemplary embodiment.

Referring now to FIGS. 3-5, various views of a first embodiment of the dressing 104 is shown. FIG. 3 shows a top view of the dressing 104 and FIGS. 4-6 show various cross-sectional views of the dressing 104.

In FIGS. 3-5, the dressing 104 is shown to include a first manifold layer 300, a second manifold layer 302, a first barrier layer 304 that is adjacent to (e.g., abuts) the first manifold layer 300, and a second barrier layer 306 abuts the second manifold layer 302. The first manifold layer 300 and the second manifold layer 302 are positioned between the first barrier layer 304 and the second barrier layer 306. In some embodiments, the first manifold layer 300 is coupled to the first barrier layer 304 by an adhesive and/or the second manifold layer 302 is coupled to the second barrier layer 306 by an adhesive.

The dressing 104 is also shown to includes a first fenestrated film layer 308 that abuts the first manifold layer 300 with and a second fenestrated film layer 308 that abuts the second manifold layer 302. The first manifold layer 300 is positioned between the first fenestrated film layer 308 and the first barrier layer 304, and the second manifold layer 302 is positioned between the second fenestrated film layer 310 and the second barrier layer 306. In some embodiments, the first fenestrated film layer 308 is coupled to the first manifold layer 300 by an adhesive and/or the second fenestrated film layer 310 is coupled to the second manifold layer 302 by an adhesive. In preferred embodiments. The first fenestrated film layer 308 is configured to be easily separated from the second fenestrated film layer 310. That is, the first fenestrated film layer 308 and the second fenestrated film layer 310 are configured to not adhere to one another.

As illustrated in FIG. 5, the first manifold layer 300, the second manifold layer 302, the first barrier layer 304, the second barrier layer 306, the first fenestrated film layer 308, and the second fenestrated film layer 310 are hand-shaped. That is, each of the layers 302-310 includes a central region 312 and five peninsular projections 314 that extend from the central region 312 in the shape of a hand. Each of the five peninsular projections 314 corresponds to one finger or thumb of a patient. The dressing 104 may be made available in various sizes corresponding to different hand sizes (i.e., different dimensions of the central region 312 and the peninsular projections 314 of the layers 300-310). For example, the dressing 104 may be available in a small size, a medium size, a large size, etc. to allow fitting to various patients without requiring individual/patient-specific customization.

The first barrier layer 304 is coupled to the second barrier layer 306 along a hand portion of a perimeter of the dressing 104 and separated from the second barrier layer 306 along a wrist portion 320 of the perimeter of the dressing 104. The first barrier layer 304 is not coupled to the second barrier layer 306 along the wrist portion 320 of the perimeter of the dressing 104, which creates an opening that allows a patient's hand to be inserted into the dressing 104. In other words, the dressing 104 is formed as a glove. The dressing 104 is thereby configured to receive a patient's hand between the first fenestrated film layer 308 and the second fenestrated film layer 310.

In the example shown, the first barrier layer 304 is coupled to the second barrier layer 306 along edges of the peninsular regions 314 and the central region 312 by film welds 316, and along a portion of the perimeter of the central region by anchor welds 318. FIG. 4 shows a cross-section view of the dressing 104 including film welds 316. The film welds 316 couple the first barrier layer 304 to the second barrier layer 306 and substantially prevent air from passing between the first barrier layer 304 and the second barrier layer 306 at the film welds. For example, the first barrier layer 304 may be thermally bonded to the second barrier layer 306 at the film welds 316.

FIG. 5 shows a cross-section view of the dressing includes film welds 316 and anchor welds 318. The anchor welds 318 couple the first manifold layer, the second manifold layer 302, the first barrier layer 304, the second barrier layer 306, the first fenestrated film layer 308, and the second fenestrated film layer 310 together along portions of the perimeter of the dressing where the anchor welds 318 are present. In the example shown, the anchor welds 318 include structures (e.g., staples, pins, etc.) extending through the layers 300-310 to restrict (e.g., substantially prevent) movement of the layers 300-310 relative to one another at the anchor welds 318. In other examples, adhesive is used along the anchor welds 318 to restrict movement of the layers 300-310 relative to one another at the anchor welds 318.

The dressing 104 is also shown to include an adhesive cuff 322. Adhesive cuff 322 includes an adhesive (or multiple adhesives) configured to seal the adhesive cuff 322 to the first barrier layer 304 and the second barrier layer 306 along the wrist portion 320 of the perimeter of the dressing and to skin of a patient. The adhesive cuff 322 extends from the first barrier layer 304 and the second barrier layer 306 such that the adhesive cuff 322 is configured to be coupled to a wrist of a patient when the patient's hand is inserted into the dressing 104. When the adhesive cuff 322 is sealed to a patient's wrist, the first barrier layer 304, and the second barrier layer 306, the adhesive cuff 322 substantially prevents air from flowing between an ambient environment and the interior of dressing 104 (e.g., the manifold layers 300, 302) via the opening at the wrist portion 320 of the dressing 104. The adhesive cuff 322 may be produced as an integrated piece of the dressing 104 or may be distributed as a separate piece of a dressing kit (e.g., as an adhesive strip).

The barrier layers 304, 306 are configured to substantially prevent airflow therethrough. The barrier layers 304, 306 may include a polyurethane drape material, for example a drape material as used in a V.A.C.® Drape by Acelity. As mentioned above, the barrier layers 304, 306 are sealed with a substantially-airtight seal by film welds 316. Accordingly, when the adhesive cuff 322 is sealed around the wrist of a patient and the barrier layers 304, 306, a substantially airtight volume is created within the dressing 104, i.e., between the barrier layers 304, 306 and the patient's hand. The barrier layers 304, 306 may each have a thickness in a range between approximately 80 and 120 microns.

As shown in FIG. 3, the first barrier layer 304 includes knuckle flexion points 324 arranged at positions that correspond to knuckles/joints within a typical hand that may be inserted into the dressing 104. In the example shown, each peninsular portion 314 corresponding to a finger includes three knuckle flexion points 324, while the peninsular portion 314 corresponding to a thumb includes two knuckle flexion points. FIG. 6 shows cross sectional views of a knuckle flexion point 324, includes a first view 600 of the knuckle flexion point 324 in an unflexed state and a second view 602 of the knuckle flexion point 324. As illustrated by FIG. 6, each knuckle flexion point 324 includes a series of folds (e.g., three folds) which, in the unflexed state, draw the barrier layer 304 away from the manifold layer 300. In the flexed state, the series of folds are extended (unfolded) to facilitate curvature (bending) of the dressing 104 at the knuckle flexion point 324 by increasing an effective length of the barrier layer 304. Accordingly, the knuckle flexion points 324 are configured to facilitate articulation, movement, etc. of a patient's fingers confined in the dressing 104. The fenestrated film layers 308, 310 and the manifolding film layers 300, 302 may be configured to resiliently stretch and/or flex to accommodate articulation, movement, etc. of a hand in the dressing 104 as shown in FIG. 6.

The fenestrated film layers 308, 310 are made of a non-adherent film and are configured to provide a non-adherent interface between the dressing 104 and a hand of a patient, including a wound bed located on the hand. The fenestrated film layers 308, 310 are also configured to prevent ingrowth of skin to the dressing (e.g., healing into the manifold layers 300, 302). The fenestrated film layer 308, 310 thereby facilitate easy insertion of a hand into the dressing 104 and removal of the hand from the dressing 104. Additionally, the fenestrated film layers 308, 310 have fenestrations (perforations, holes, airways, windows, etc.) extending therethrough that allow air and fluid to pass between the hand (e.g., a wound bed) and the manifold layers 300, 302. The fenestrated film layers 308 may each have a thickness of approximately 30 microns.

The manifold layers 300, 302 are configured to allow air and fluid to flow therethrough. The manifold layers are made of an open-cell foam, for example a reticulated polyurethane open cell foam. In some embodiments, the manifold layers 300, 302 are made of an open-cell foam marketed as GRANUFOAM™ by ACELITY™. The manifold layers 300, 302 may each have a thickness in a range between approximately 6 mm and 10 mm. Accordingly, the manifold layers 300, 302 may be thinner than in conventional bulky dressings. The reduced thickness of the manifold layers 300, 302 facilitates flexion of the dressing 104 to allow for physiotherapy for the hand in the dressing 104 in a way not previously achieved.

The manifold layers 300, 302 allow for the communication of air pressure, for example negative pressure (relative to ambient air pressure), through the manifold layers 300, 302 and to the hand and the wound bed (via the fenestrated film layers 308, 310. The dressing 104 is configured such that air and fluid can flow between the first manifold layer 300 and the second manifold layer 302 proximate the film welds 316 and anchor welds 318, i.e., through the fenestrated film layers 308, 310 and around a hand positioned in the dressing 104. Negative pressure can thereby be communicated across both manifold layers 300, 302 (i.e., such that both manifold layers 300, 302 are maintained at approximately equal pressures).

The dressing 104 is configured to be coupled to a vacuum (negative pressure) tube 106 and, in some embodiments, an instillation tube 108. For example, a hole may be cut in the first barrier layer 304 (e.g., with a diameter in a range between approximately 3-20 mm) and a connection pad may be coupled to the barrier layer 304 over the hole. The connection pad is coupled to the vacuum tube 106 and/or instillation tube 108. In some embodiments, multiple holes and/or connection pads are used. For example, the connection pad may be a SENSAT.R.A.C.™ connection pad marketed by ACELITY™.

The manifold layers 300, 302 can thereby be put in fluid communication with the vacuum tube 106 and/or instillation tube 108. As described above with reference to FIGS. 1-2, the negative pressure pump 112 can be controlled to remove air from the manifold layers 300, 302 to establish a negative pressure at the manifold layers 300, 302. The negative pressure at the manifold layers 300, 302 is communicated to the hand/wound via the fenestrations in the fenestrated film layers 308, 310. Instillation fluid may also be provided to the wound via the manifold layers 300, 302 and the fenestrated film layers 308. Wound exudate, instillation fluid, other debris, etc. may also be removed from the wound and manifold layers via the vacuum tube 106 as described above with reference to FIGS. 1-2. The dressing 104 thereby facilitates treatment of a hand wound using NPWTi.

Still referring to FIGS. 3-6, the dressing 104 is also shown to include one or more sensor(s) 204. positioned on the first barrier layer 304. In the embodiment shown, the one or more sensor(s) include a humidity sensor and a moisture sensor, which may be positioned extending through the first barrier layer 304 to measure humidity and moisture in the first manifold layer 300. In some embodiments, the one or more sensor(s) include one or more pH sensor(s) configured to measure tissue pH and/or fluid pH. In the embodiment shown, the one or more sensor(s) also include a strain sensor 326. The strain sensor 326 is positioned on or in the first barrier layer 304 and extends along a length of the dressing from proximate the wrist portion 320 to a tip of one of the peninsular regions 314 (e.g., corresponding to a middle finger). The strain sensor 326 is configured to measure (e.g., generate an electrical signal indicative of) a strain on the dressing 104 (i.e., on the strain sensor 326), which may correspond to a curvature of the dressing 104 and/or a force applied by the hand inside the dressing 104. For example, a strain measured by the strain sensor 326 may increase when a patient attempts to clench the hand (e.g., in a fist) or otherwise bend one or more fingers in the dressing 104. The strain may decrease when the patient moves the hand in the dressing 104 to an open or neutral pose. The one or more sensors 204 include a wireless communications circuit (e.g., WiFi transceiver, Bluetooth transceiver, etc.) configured to facilitate wireless transmission of measurements from the one or more sensors to the control circuit 202 of the therapy unit 102.

Figure 7:
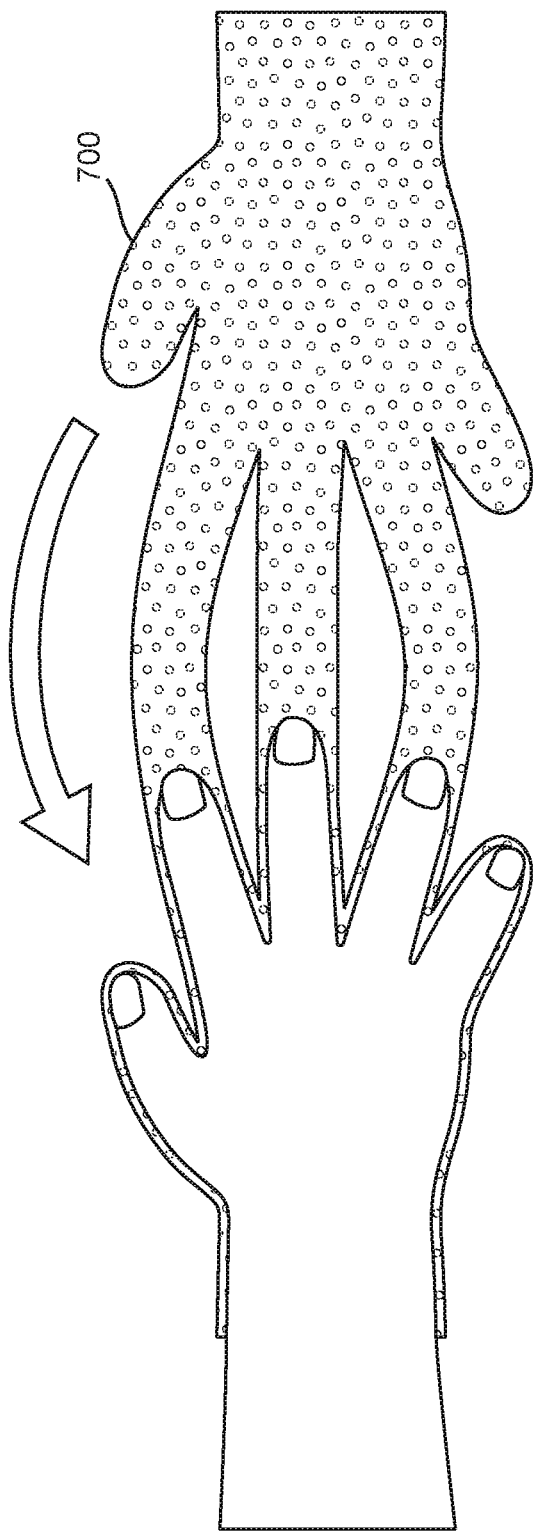
FIG. 7 is an illustration of a wound-dressing interface for use with a glove-shaped dressing used with the NPWTi system of FIGS. 1-2, according to an exemplary embodiment.
Figure 9:
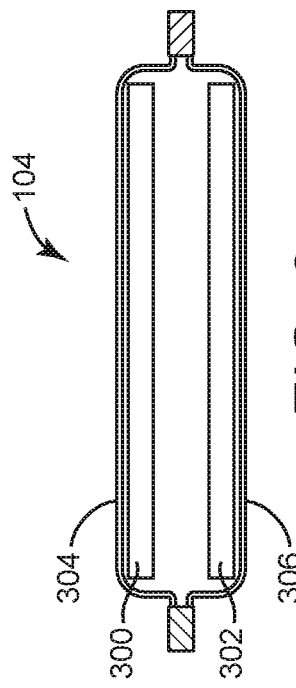
FIG. 9 is a cross-section view of the glove-shape dressing for use with the wound-dressing interface of FIG. 7, according to an exemplary embodiment.
Figure 8:
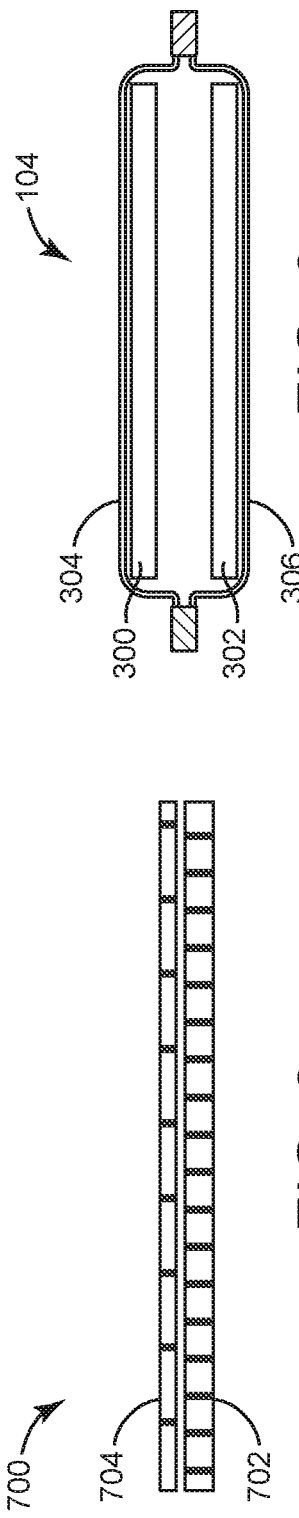
FIG. 8 is a cross-section view of the wound-dressing interface of FIG. 7, according to an exemplary embodiment.

Referring now to FIGS. 7-9, a second embodiment of the dressing 104 is shown, according to an exemplary embodiment. In FIGS. 7-9, the non-adhesive fenestrated film layers 308, 310 are omitted from the dressing 104, such that the dressing 104 is formed as a glove including the barrier layers 304, 306 and the manifold layers 300, 302 arranged as described above. A wound-dressing interface 700 is also included as a separate piece (i.e., distributed to caregivers/patients as a separate piece in a dressing kit that also includes the glove-shaped dressing 104 formed from the barrier layers 304, 306 and the manifold layers 300, 302). The wound-dressing interface 700 is formed as a single piece (sheet) as shown in FIG. 4, for example shaped within peninsular extensions and or bridge/isthmus-shaped portions configured to be aligned with fingers of a patient when the wound-dressing interface 700 is folded over a patient's hand.

The wound-dressing interface 700 includes a patient interface layer 702 and a foam interface layer 704. The foam interface layer 704 includes a fenestrated film, for example a polyurethane or polyethylene film with fenestrations extending therethrough. The foam interface layer 704 allows air and fluid to flow therethrough and limits adherence of the wound-dressing interface 700 to the manifold layers 300, 302. The patient interface layer 702 includes a perforated silicone and a hydrogel or polyurethane gel. The patient interface layer 702 is configured to adhere to itself. In some embodiments, the patient interface layer 702 is configured to adhere to skin.

The wound-dressing interface 700 is thereby configured to be folded over a hand and adhered to itself (mated to itself) to substantially enclose the hand in the wound dressing interface 700 such that the patient interface layer 702 faces inwards (i.e., towards the hand) and the foam interface layer 704 faces outwards (i.e., away from the hand). The hand and the wound-dressing interface 700 can then be inserted into the glove portion of the dressing 104, i.e., the barrier layers 304, 306 and the manifold layers 300, 302 arranged as described above (and as shown in FIGS. 9 and 3). With the hand enclosed in the wound-dressing interface 700, the wound-dressing interface 700 prevents direct contact between the hand and the manifold layers 300, 302 while allowing air and fluid to pass through fenestrations in the wound-dressing interface 700. The adhesive cuff 322 can then be applied around the patient's wrist to seal the dressing 104 around the hand as described above. To further prepare the dressing 104 for NPWTi, a hole can be cut in a barrier layer 304, 306 and a connection pad coupled to the barrier layer 304, 306 over the hole to place a vacuum tube 106 and/or an instillation tube 108 in fluid communication with the manifold layers 300, 302. The therapy unit 102 can then be operated as described above to establish negative pressure at the hand and/or provide instillation fluid to the hand.

The embodiments of FIGS. 3-9 show glove-shaped dressings, i.e., with individually-differentiated fingers (e.g., as formed by peninsular projections 314). Other embodiments of the dressing 104 may be mitten-shaped, i.e., with a unified area for four fingers and a separate projection for a thumb. Such mitten-shaped dressings may otherwise be configured as described herein for the glove-shaped dressings of FIGS. 3-9. Other variations are also contemplated by the presented disclosure, for example a three-compartment glove where the two pairs of fingers each share a compartment and the thumb has a compartment, etc. All such variations are within the scope of the present disclosure.

Figure 10:
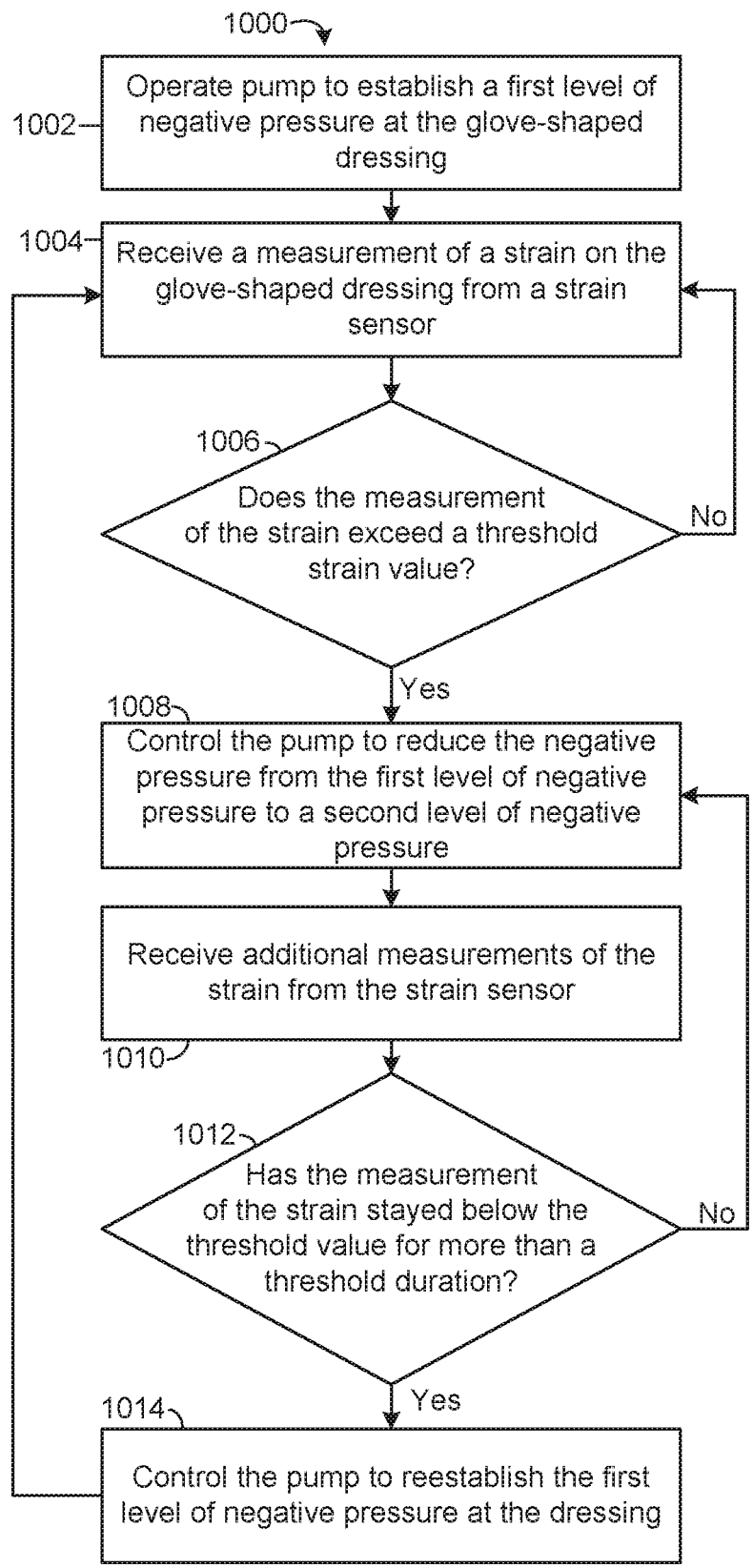
FIG. 10 is a flowchart of a process for providing a physiotherapy mode with the NPWTi system of FIGS. 1-2, according to an exemplary embodiment.
Figure 11:
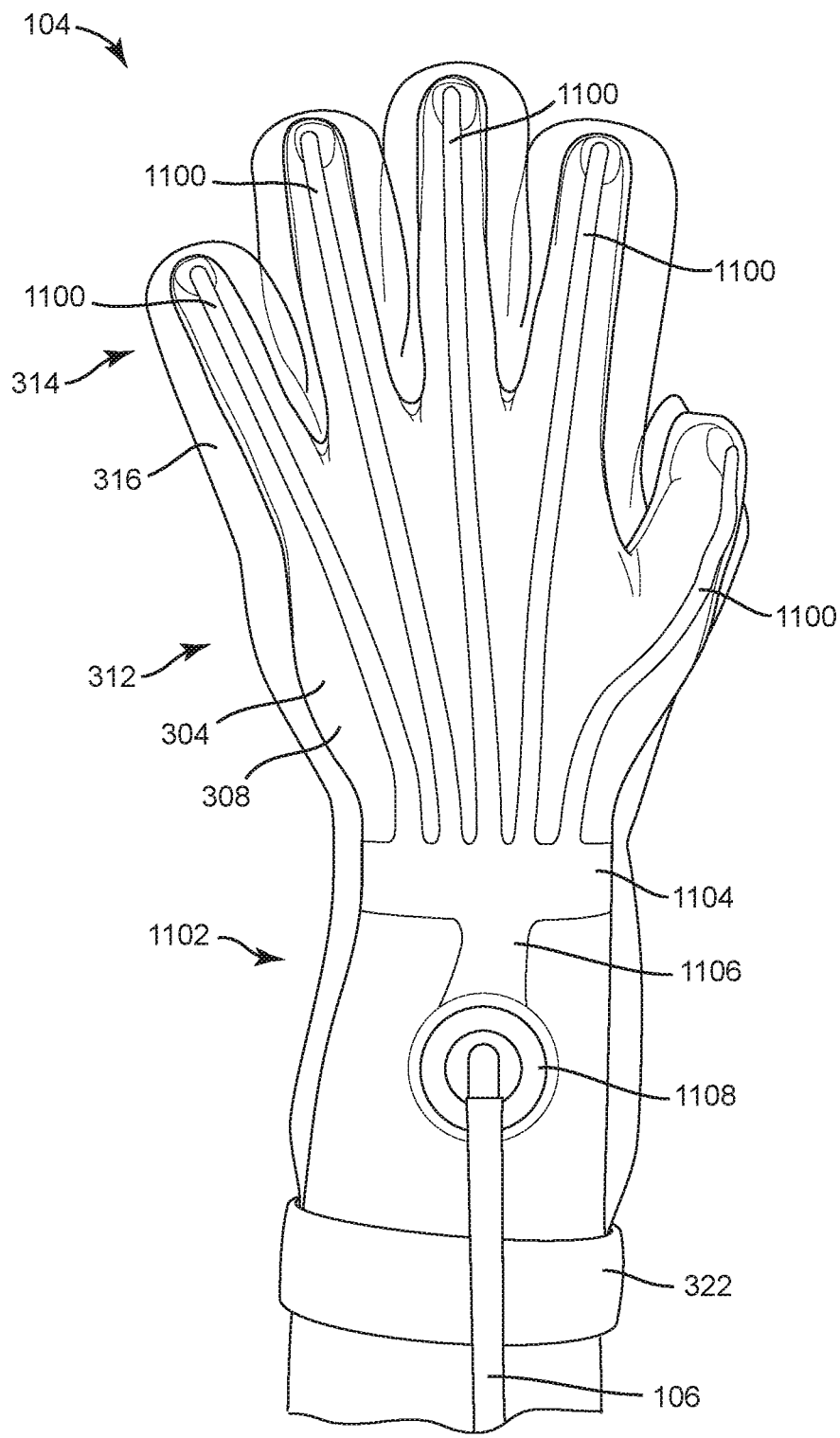
FIG. 11 is a first perspective view of a dressing for treating a hand wound and for use with the NPWTi system of FIGS. 1-2, according to an exemplary embodiment.
Figure 12:
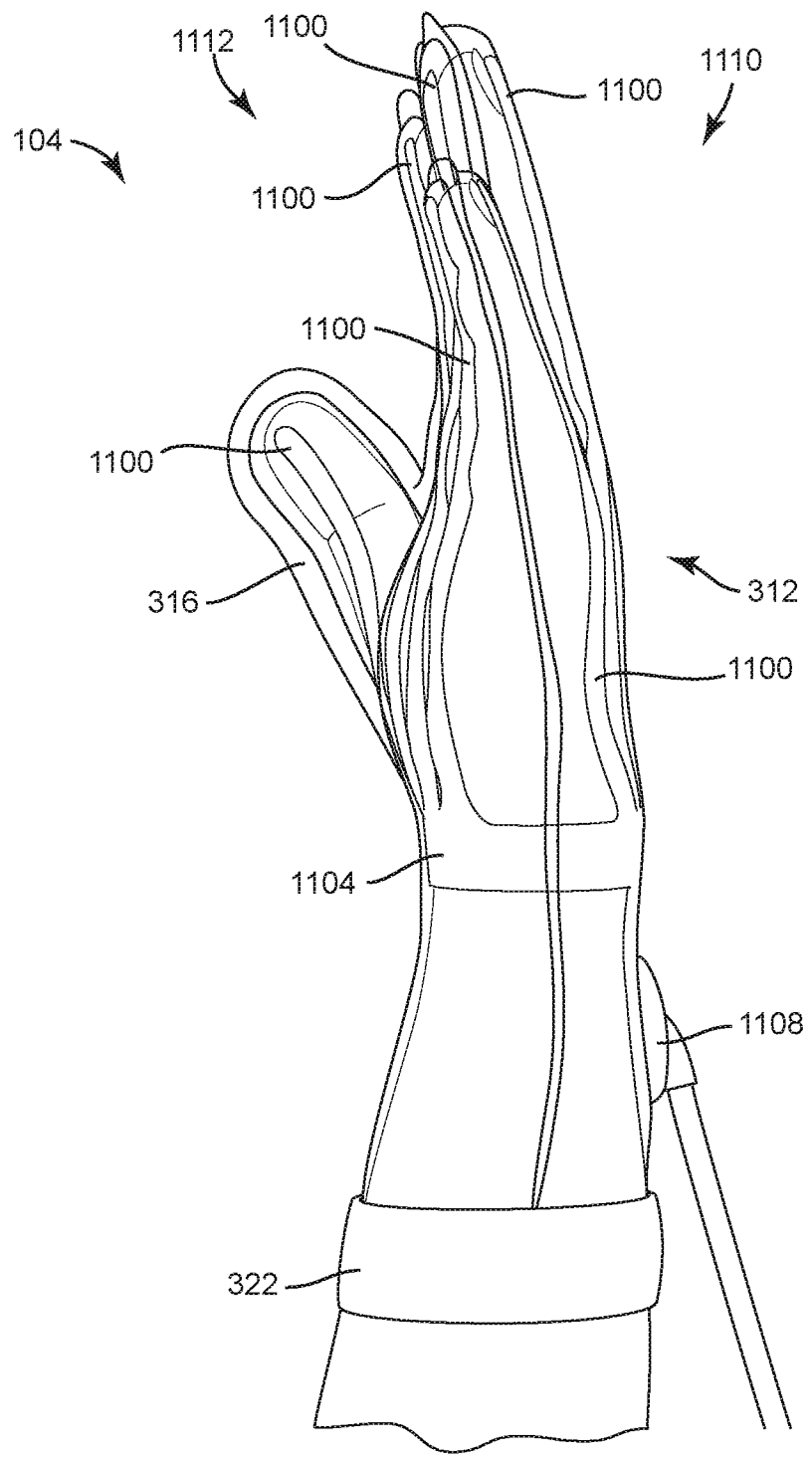
FIG. 12 is a second perspective view of the dressing of FIG. 11, according to an exemplary embodiment.
Figure 13:
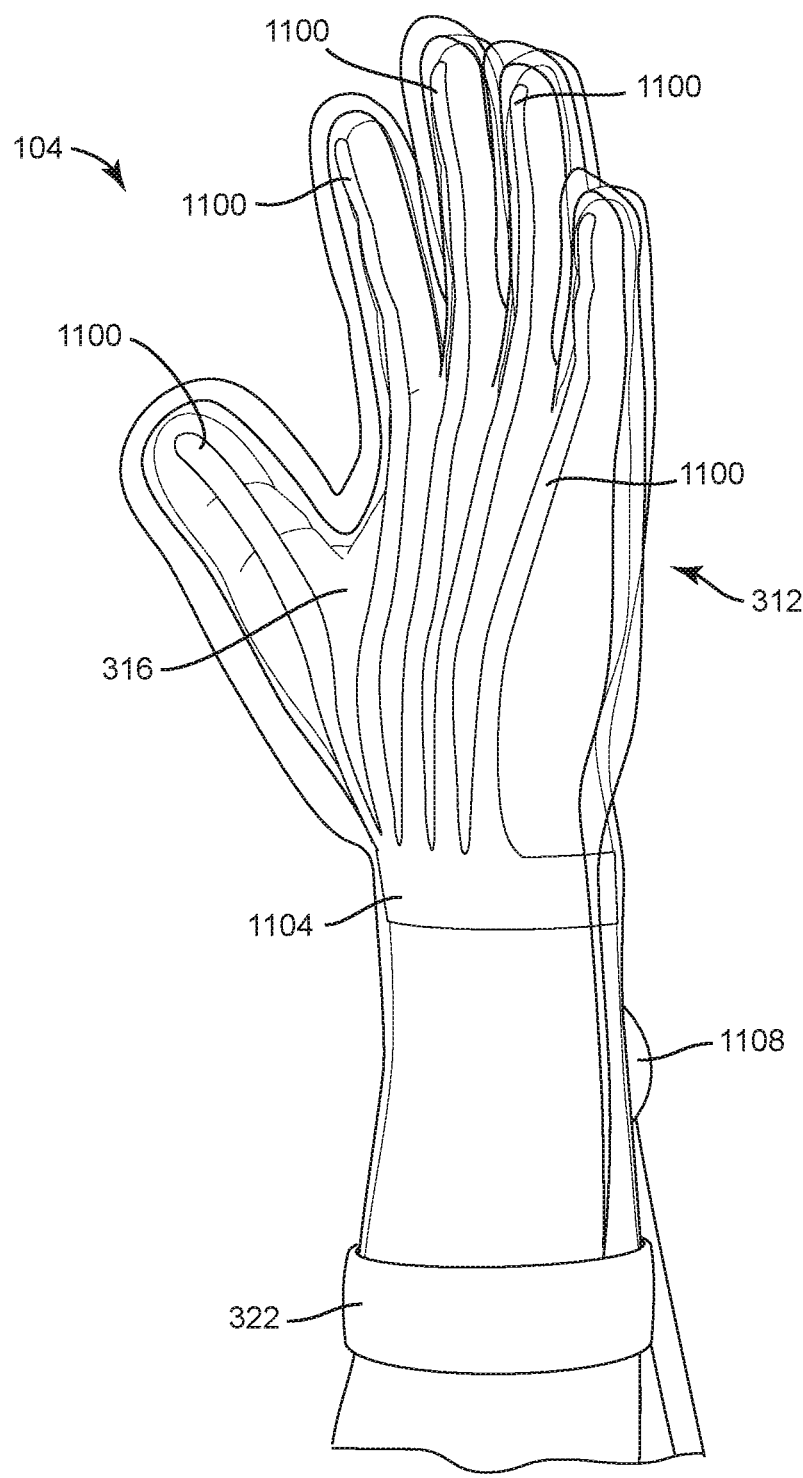
FIG. 13 is a third perspective view of the dressing of FIG. 11, according to an exemplary embodiment.
Figure 14:
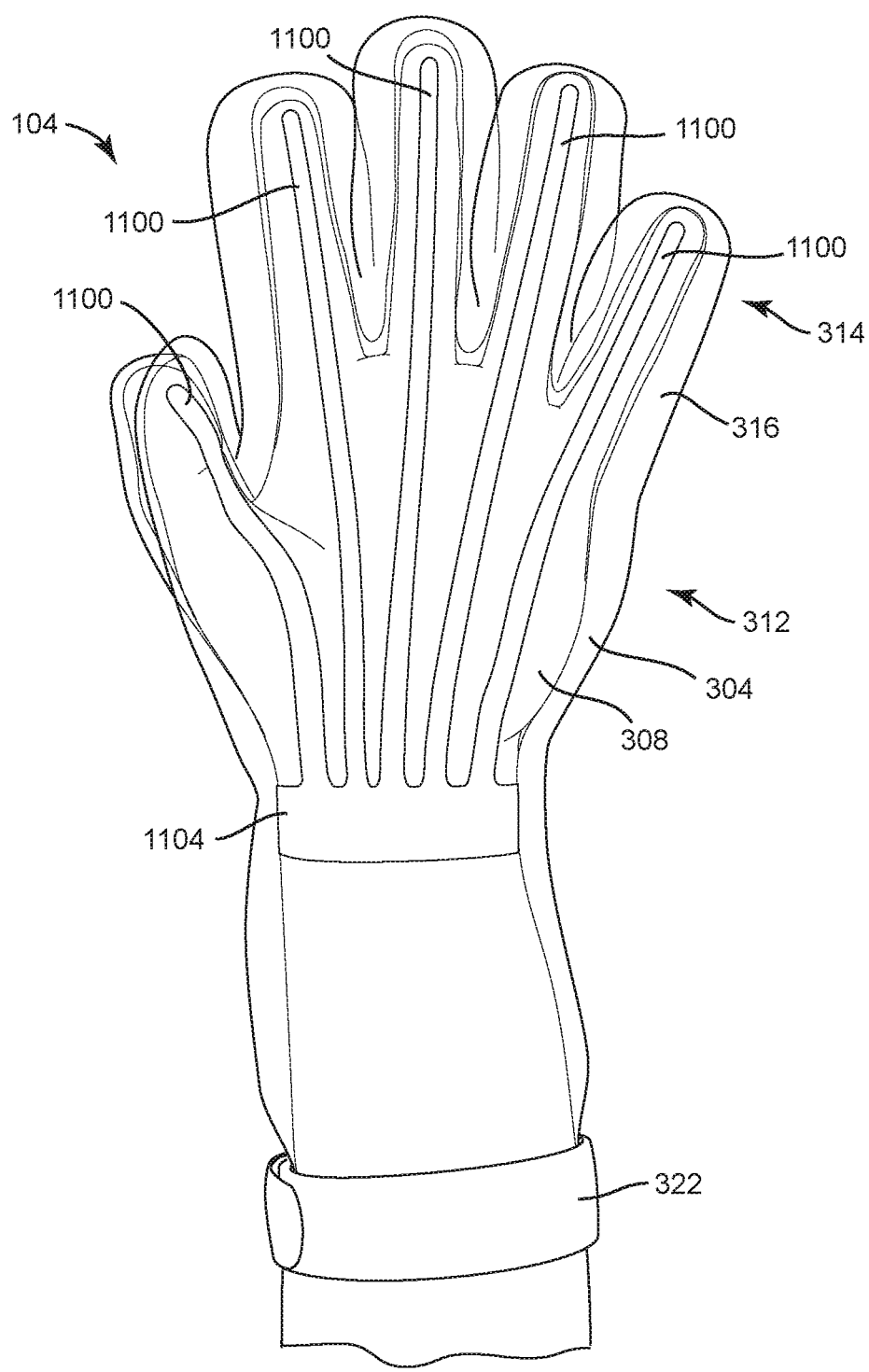
FIG. 14 is a fourth perspective view of the dressing of FIG. 11, according to an exemplary embodiment.

Referring now to FIG. 10, a process 1000 of providing a physiotherapy mode with the NPWTi system 100 of FIG. 1-2 and the hand dressing 104 of FIGS. 3-9 is shown, according to an exemplary embodiment. Process 1000 provides a physiotherapy mode that allows movement, articulation, bending, etc. of a hand in the dressing 104 during NPWTi treatment. Accordingly, execution of process 1000 facilitates a patient in redeveloping strength, neuromuscular activity, coordination, etc. in the hand while the dressing 104 is applied to the hand. Additionally, movement of the hand as provided for by process 1000 reduces the risk of contracture, i.e., the risk that the skin may heal too tight such that the patient's skin restricts the range of motion of the joints in the hand. Movement, articulation, etc. of the fingers and hand during wound healing may facilitate proper healing that allows for a full range of motion of the hand after wound healing. Process 1000 can be executed by the control circuit 202 of the therapy unit 102.

At step 1002, the negative pressure pump 112 is operated to establish a first level of negative pressure at the glove-shaped dressing 104. The first level of negative pressure may correspond to a preferred level for negative pressure wound therapy, for example in the range of approximately 100 mmHg to 175 mmHg of negative pressure. When the first level of negative pressure is applied, the pressure differential between the ambient air and the interior of the dressing 104 increases the rigidity of the dressing 104 such that dressing 104 substantially restricts (limits, prevents, etc.) articulation of the hand.

At step 1004, a measurement is received from the strain sensor 326 on the glove-shaped dressing 104. The measurement includes a current value of a strain on the dressing 104. The strain on the dressing 104 may correspond to an amount of force exerted on the dressing 104 by the hand in the dressing 104 in an attempt to curl, bend, articulate, etc. the fingers in the dressing 104. The measurement may be received by the control circuit 202 via a wireless network (e.g., Bluetooth communications, WiFi communications, etc.).

At step 1006, the measurement is compared to a threshold strain value. The threshold strain value may be predetermined, for example by bench testing. The threshold strain value corresponds to a significant probability that the patient is deliberately attempting to articulate the hand in the dressing 104. In the measurement does not exceed the threshold measurement, pump 112 continues to be controlled to provide the first level of negative pressure at the dressing 104 while more measurements of the strain are received at the control circuit 202 over time.

If a determination is made that the measurement of the strain exceeds the threshold strain value, a physiotherapy mode is initiated at step 1008. At step 1008, the pump 112 is controlled (e.g., by the control circuit 202) to reduce the negative pressure from the first level of negative pressure to a second level of negative pressure. The second level of negative pressure is "lower" than the first level of negative pressure, i.e., closer to atmospheric pressure (e.g., in a range of approximately 25 mmHg to 75 mmHg). At the second level of negative pressure, the rigidity of the dressing 104 is lower than at the first level of negative pressure. Accordingly, at the second level of negative pressure, the dressing 104 and the NPWIT system 100 allows the patient to at least partially bend, articulate, move, etc. the fingers and hand in the dressing 104. For example, the patient may follow guided instructions from a therapist. In some embodiments, the therapy unit is configured to provide instructions for a physiotherapy routine to a user via the input/output device 118.

At step 1010, additional measurements of the strain are received from the strain sensor 234. As the patient continues to articulate the hand in the dressing 104, the strain will stay above the threshold strain value and/or repeatedly exceed the threshold strain value. At step 1012, a determination is made of whether the measurement has fallen below the threshold strain value for at least a threshold duration of time. The threshold duration of time may be selected as indicative that the patient has ended a physiotherapy routine or other attempt to articulate the hand in the dressing 104. If the strain has not fallen below the threshold strain value for at least the threshold duration of time, the pump 112 continues to be controlled to maintain the second level of negative pressure at the dressing.

If the strain has fallen below the threshold strain value for at least the threshold duration of time, the pump 112 is controlled to reestablish the first level of negative pressure at the dressing at step 1014, i.e., to reestablish an optimal NPWTi regime and exit the physiotherapy mode. The process may then return to step 1004 where the strain measurements are monitored. Repeated iterations of the physiotherapy mode may thereby be initiated and exited to facilitate both physiotherapy and NPWTi for the hand in the dressing 104 over time. With the advantages described above, the dressing 104 may be well-suited for long-term application to the hand (e.g., seven days or longer).

Several variations on the process 1000 are also contemplated by the present disclosure. For example, in some embodiments, the physiotherapy mode can be initiated or ended in response to user input to the input/output device 118 commanding a start or end to the physiotherapy mode. As another example, the control circuit 202 may prevent execution of the process 1000 (e.g., prevent initiation of physiotherapy mode) during an instillation cycle (e.g., while instillation fluid is being supplied to the dressing 104). As another example, in some embodiments, a dynamic pressure control mode (e.g., cyclic variations in negative pressure) is applied outside of the physiotherapy mode (e.g., in place of the first level of negative pressure). Various such variations are possible.

Additionally, although the embodiments described herein are designed for use on hands, variations suitable for use on feet or amputation stumps are also within the scope of the present disclosure. For example, a variation suitable for use on a foot may be formed as a sock, with or without a separate pocket/projection for each toe, rather than as a glove as shown for the hand dressings described above. Variations of the dressing 104 can therefore be tailored for use in treating wounds in many anatomical locations.

The dressing 104 and NPWTi system 100 described above provide various advantages over existing dressings and wound therapy systems. The dressing 104 is easy to apply (thereby reducing application time) and remove without damaging the healed/healing wound (e.g., by avoiding a risk of in-growth into the dressing structure). The dressing 104 and NPWTi system 100 also allow for effective positioning of the dressing 104 while also allowing early movement in the full range of motion (or at least a significant portion of the range of motion) of the wounded/treated hand. The dressing 104 and NPWTi system 100, in the embodiments shown, are suitable for providing negative pressure and instillation therapy for up to at least seven days. The dressing 104 may reduce the use of foam relative to existing dressings, thereby making the dressing 104 smaller and less cumbersome for the patient. The dressing 104 and the NPWTi system 100, in the embodiments shown, also provide for an automatic physiotherapy mode that facilitates rehabilitation and reduces the risk of contractures. Additionally, the dressing 104 includes sensors that wirelessly (e.g., without the annoyance/complication of additional cables/wires/etc.) communicate useful measurements/diagnostics to a caregiver that allow early detection of infection or other developments in wound treatment. Therefore, the dressing 104 and NPWTi system 100 disclosed herein provide many advantages over existing systems that can improve outcomes for patients while also improving the overall treatment experience.

Figure 15:
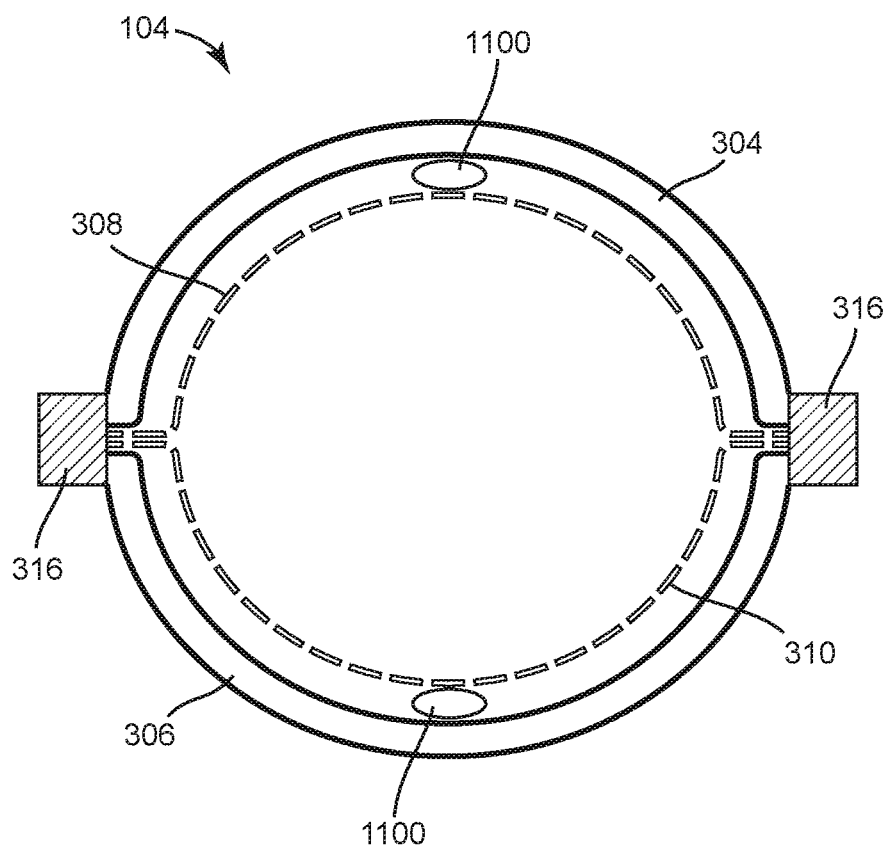
FIG. 15 is a cross-sectional view of the dressing of FIG. 11, according to an exemplary embodiment.
Figure 16:
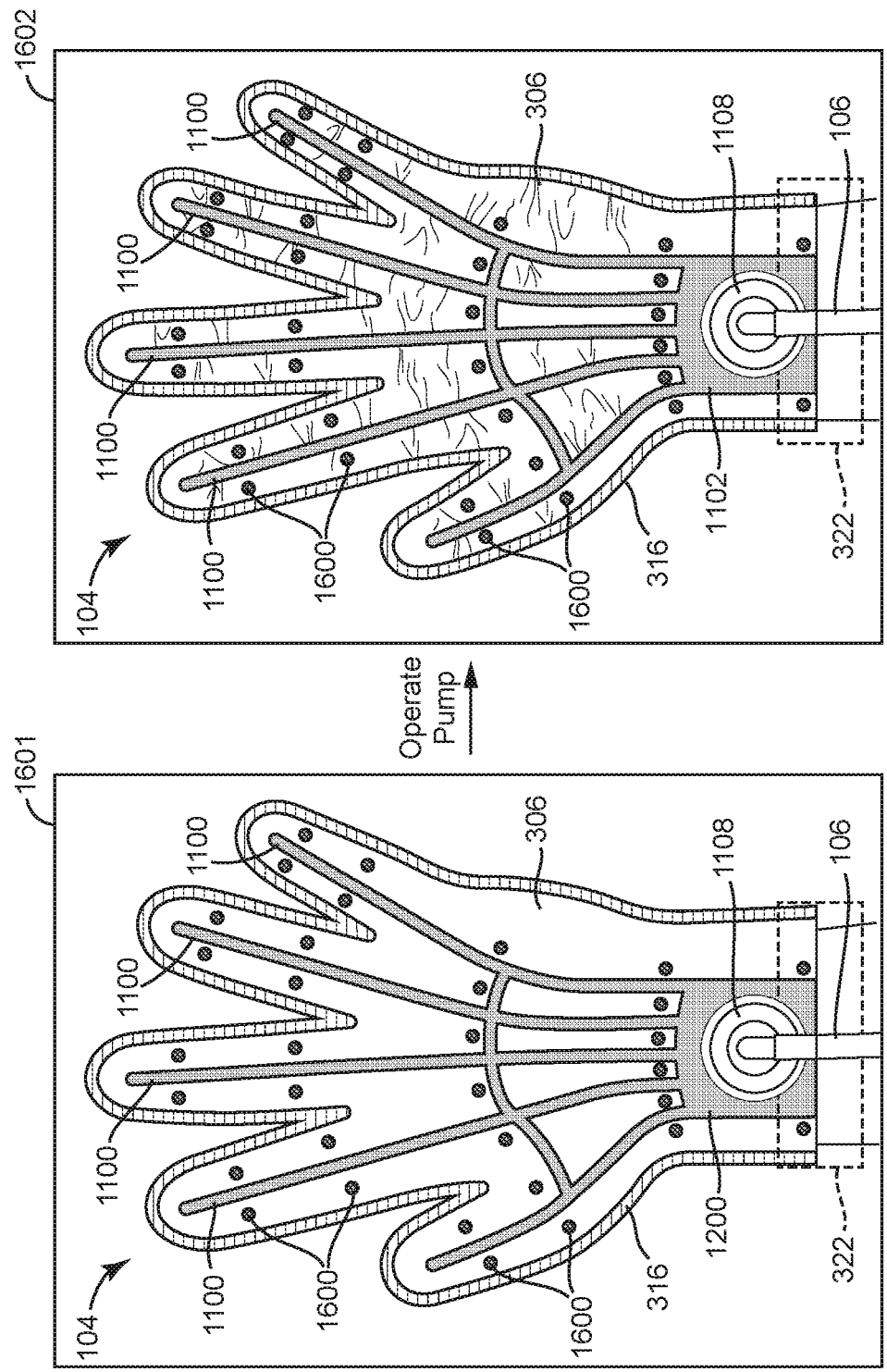
FIG. 16 is an illustration of a process of operating the NPWTi system of FIGS. 1-2 with the dressing of FIG. 11, according to an exemplary embodiment.

Referring now to FIGS. 11-16, another embodiment of the dressing 104 is shown, according to exemplary embodiments. FIGS. 11-14 show various perspective views of the dressing 104. FIG. 15 shows a cross-sectional view of the dressing 104. FIG. 16 illustrates an advantageous behavior of the dressing 104 when air is removed from the dressing 104. The dressing 104 as in FIGS. 11-16 may include some or all of the various features and advantages of the dressing 104 in the embodiments described above, with some differences as described in detail below. Advantageously, as shown in FIGS. 11-16, the dressing 104 includes transparent or translucent portions such that a patient or caregiver can visually assess a wound without removing the dressing 104 from the patient's hand.

As shown in FIGS. 11-16, the manifold layers 300, 302 are formed as multiple felted foam strips 1100 which extend from a felted foam pad 1102. Each felted foam strip extends from the central region 312 of the dressing to one of the multiple peninsular projections 314. In other words, each "finger" (including the "thumb") of the dressing 104 has a corresponding felted foam strip 1100 aligned therewith. In the example shown, both a first side 1110 of the dressing 104 (corresponding to a back of the hand) and a first side 1112 of the dressing 104 (corresponding to the palm of the hand) include felted foam strips 1100. Accordingly, in this example, two felted foam strips 1100 are aligned with each of the peninsular projections 314 (i.e., one felted foam strip 100 on the first side 1110 and one felted foam strip 1100 on the first side 1112). It should be understood that various arrangements, numbers, patterns, webs, lattices, etc. of felted foam strips 1100 are possible in various embodiments.

In the example of FIGS. 11-14, the felted foam pad 1102 includes a wrist strap 1104 and a connection surface 1106. The wrist strap 1104 (e.g., felted foam cuff) is located at a wrist region of the dressing 104 and connects the felted foam strips 1100 of the first side 1110 with the felted foam strips 1100 of the first side 1112, thereby allowing air and fluid to flow between the felted foam strips 1100 of the first side 1110 and the felted foam strips 1100 of the second side (e.g., to facilitate communication of negative pressure between the first side 1110 and the first side 1112).

The connection surface 1106 provides an area of felted foam having a sufficient surface area to allow connection of the dressing 104 to the tube 106 in fluid communication with the manifolding layer 300 (i.e., with the wrist strap 1104 and the felted foam strips 1100). In the example shown, the felted foam strips 1100 and the wrist strap 1104 may be narrow (e.g., having a width less than a diameter of a connection pad 1108 which couples the dressing 104 to the vacuum tube 106 and, in some embodiments, to the instillation tube 108. The connection surface 1106 provides a larger surface area (e.g., having a diameter equal to or larger than the diameter of the connection pad 1108; having a diameter in a range between approximately ten millimeters and approximate twenty-five millimeters, for example approximately twenty millimeters; etc.) which allows the tube 106 to be placed in fluid communication with the manifolding layer 300. In the example shown in FIG. 11, the connection surface 1106 of the felted foam pad 1102 is located along a forearm region of the dressing 104, such that the connection pad 1108 is positioned at a non-articulating anatomical feature when applied to a patient. The connection surface 1106 thereby provides a convenient, comfortable, and effective position at which the connection pad 1108 can be coupled to the dressing 104.

As shown in FIG. 15 and consistent with the embodiment of FIGS. 4-5 described above, the dressing 104 includes as a first manifold layer 300 (shown as a felted foam strip 1100), a second manifold layer 302 (also shown as a felted foam strip 1100), a first barrier film layer 304, a second barrier film layer 306, a first fenestrated film layer (wound contact layer) 308, and a second fenestrated film layer (wound contact layer) 308. The first manifold layer 300 is positioned between the first fenestrated film layer 308 and the first barrier layer 304, and the second manifold layer 302 is positioned between the second fenestrated film layer 310 and the second barrier layer 306. The first manifold layer 300, the first fenestrated film layer 308, and the first barrier film layer 304 form a first side 1110 of the dressing 104. The second manifold layer 302, the second fenestrated film layer 310, and the second barrier layer 306 form a second side of the dressing 104. In some embodiments, the first side 1110 and/or the first side 1112 are thermoformed to have a domed cross section to match the anatomical curvature of a hand, thereby improving fit, aesthetics, and comfort of the dressing 104.

In the example of FIGS. 11-16, the first manifold layer 300 and second manifold layer 302 are formed as felted foam strips 1100 that occupy only a portion (i.e., less than an entirety) of the surface area of the barrier film layers 304, 306 and only a portion (i.e., less than an entirety) of the surface area of the fenestrated film layers 308, 310. The felted foam strips 1100 may have a width in a range of approximately two millimeters to ten millimeters, and may have a thickness in a range of approximately one millimeter to two millimeters. In regions of the dressing 104 unoccupied by the felted foam strips 1100, the first barrier film layer 304 is adjacent to (e.g., abutting) the first fenestrated film layer 308 and the second barrier film layer 306 is adjacent to the second fenestrated film layer 310.

In some embodiments, the barrier film layers 304, 306 and the fenestrated film layers 308 are transparent or translucent. In such embodiments and in regions unoccupied by the felted foam strips 1100, the dressing 104 can be transparent or translucent. Accordingly, in the embodiments of FIGS. 11-16, the dressing 104 is configured to allow a patient or caregiver to visually assess (see, optically inspect, etc.) a wound through the dressing 104 without removal or modification of the dressing 104. The dressing 104 thereby facilitates a caregiver or patient in monitoring wound healing and, in some cases, making adjustments to wound therapy based on such monitoring.

The first side 1110 and the first side 1112 may be coupled together by welds 316 and/or 318 around a perimeter of the dressing 104 with the exception of an opening at a wrist portion 320 of the perimeter of the dressing 104 (e.g., as described above with reference to FIGS. 3-5). In the examples of FIGS. 11-16, spot welds 1600 may also be included and distributed between and around the felted foam strips 1100. At the first side 1110, the first barrier film layer 304 is coupled (e.g., welded, adhered) to the first fenestrated film layer 308. At the first side 1112, the second barrier film layer 306 is coupled to the second fenestrated film layer 310. The spot welds 1600 may be placed to partially constrain movement of the of the felted foam strips 1100. For example, spot welds 1600 may be placed slightly apart from the felted foam strips 1100 such that the felted foam strips 1100 are allowed to move, bend, translate, slide, etc. within a limited range of positions relative to the barrier film layer 304/306 and the fenestrated film layer 308/310. In some cases, the spot welds 1600 ensure that the felted foam strips 1100 remain substantially aligned with the peninsular (finger, thumb) regions 314 while allowing for some movement and repositioning which facilitates the dressing 104 in conforming to a particular patient's hand, provides flexibility to the dressing 104, and facilitates articulation of the patient's hand while the dressing 104 is applied to the hand. In other embodiments, an adhesive can be included to couplet the felted foam strips 1100 to the barrier film layer 304/306 and/or the fenestrated film layer 308/310.

FIG. 16 illustrates application and use of the dressing 104 of FIGS. 11-15 in a two-frame storyboard depiction. As illustrated in the first frame 1601, the dressing 104 is placed onto a patient's hand and the adhesive cuff 322 is applied to seal the dressing 104 around the patient's wrist or forearm. In various embodiments, the dressing 104 may include a wrist/forearm region of various lengths (i.e., to extend along a forearm of a patient), such that the opening may align with various locations on the forearm of the patent in various embodiments. The dressing 104 may be sized slightly larger than the hand to facilitate insertion of the hand into the dressing 104. When the adhesive cuff 322 is sealed around the opening in the dressing 104 and the patient's wrist or forearm, a substantially-airtight internal volume is created between the dressing 104 and the hand.

To transition from the first frame 1601 to the second frame 1602, the negative pressure pump 112 is operated to remove air and/or other fluids or debris from the dressing 104 via the tube 106, the connection pad 1108, the felted foam pad 1102, and the felted foam strips 1100 to establish a negative pressure within the dressing 104 and at the hand (e.g., at a wound). Operating the negative pressure pump 112 results in a reduction in volume of the dressing 104 as the dressing 104 is pulled inwards towards the hand by the pressure differential across the barrier film layers 304, 306.

As illustrated in the second frame 1602, the reduction in volume of the dressing 104 in response to operation of the negative pressure pump 112 results in the formation of wrinkles (creases, folds, etc.) in the barrier film layers 304, 306 and the fenestrated film layers 308, 310. The wrinkles may form with openings, gaps, channels, airways, etc. in and across the wrinkles, such that at least a portion of the wrinkles provide manifolding pathways for air and fluid flow. For example, gaps, channels, etc. may be formed between the barrier film layers 304, 306 and the fenestrated film layers 308, 310. Furthermore, at least a portion of the wrinkles are in fluid and/or pneumatic communication with the felted film strips 1100. Accordingly, air and fluid can flow between the felted film strips 1100 and regions of the hand not directly aligned with the felted foam strips 1100.

Therefore, although the felted foam strips 1100 cover only a portion of the surface area of the dressing 104 and the hand treated thereby, the wrinkles formed by operation negative pressure pump 112 can provide air and fluid manifolding to a much larger portion of the surface area of the dressing 104 and the hand (e.g., to the substantially the entire hand). The dressing 104 thereby facilitates the establishment and maintenance of a negative pressure at the hand, removal of wound exudate and other fluid/debris from the hand, and, in some embodiments, instillation of an instillation fluid to the hand. Furthermore, as the (substantially opaque) felted foam material covers only a portion of the surface area of the dressing 104, a patient or caregiver can visually inspect a wound without removing the dressing 104, including while negative pressure is established at the hand.

In some embodiments, one or more thermo-chromic indicators are positioned on the fenestrated film layers 308, 310, for example on the inner (i.e., hand-facing) surface or outer (i.e., non-hand-facing) surface of the fenestrated film layers 308, 310. The thermo-chromic indicators are configured to change color with changes in temperature, such that the color of a thermo-chromic indictor is indicative of the temperature of the skin or wound bed proximate the thermo-chromic indicator. Because the dressing 104 of FIGS. 11-16 is translucent or transparent in various regions, such indicators may be visible through the dressing 104, thereby allowing a patient or caregiver to assess wound healing on the basis of temperature indications. Such temperature indicators may be particularly useful in assessment and treatment of burns. Multiple indicators can be used to provide temperature information at multiple locations of the dressing 104. In some embodiments, pH-chromic indicators configured to change color with changes in pH may be included with the dressing 104 and opinionated like the thermo-chromic indicators to provide information relating to the pH of the hand at various areas of the hand.

Various other embodiments of the dressing 104 are also possible. For example, in some embodiments the felted foam strips 1100 are non-felted. That is, the foam strips 1100 may be made of an open-celled polyurethane foam which may or may not be felted (e.g., heated and compressed) in various embodiments. In other embodiments, the felted foam strips 1100 are replaced by non-foam thermoformed pathways, for example tubes or other pathways formed on or coupled to the barrier film layer (e.g., formed of a polyurethane drape material). In other embodiments, various spacer materials are positioned to cause the wrinkles to form in a desired pattern, in some cases such that some or all of the felted foam strips 1100 can be omitted.

Although the embodiments herein are described with reference to a dressing shaped for a hand, the dressings, systems, and methods disclosed herein may be adapted for use with feet, amputation stumps, and other extremities. Furthermore, various combinations of the features and embodiments described herein are possible. For example, in some embodiments, the first side 1110 of the dressing 104 includes the felted foam strips as in FIGS. 11-16, while the second side 1112 includes a sold/continuous manifold layer 302 as in FIGS. 3-5 (or vice versa). Various combinations of felted foam materials, strips, pads, zones, etc. may be used to customize wound therapy. All such variations are within the scope of the present disclosure.

Configuration of Exemplary Embodiments

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

What is claimed is:

1. A dressing, comprising:
a first side of a glove assembly including:
a first barrier film layer;
a first wound contact layer coupled to the first barrier film layer; and
a plurality of first felted foam strips positioned between the first barrier film layer and the first wound contact layer, each strip providing a manifolding pathway;
wherein the first barrier film layer and the first wound contact layer comprise a central region and a plurality of peninsular projections extending therefrom in a shape of a hand, and
wherein each strip of the plurality of first felted foam strips extends from the central region to one of the plurality of peninsular projections,
a second side of the glove assembly coupled to the first side of the glove assembly, the second side of the glove assembly including:
a second barrier film layer;
a second wound contact layer coupled to the second barrier film layer; and
a plurality of second felted foam strips positioned between the second barrier film layer and the second wound contact layer, each strip providing a manifolding pathway; and
a felted foam cuff fluidly communicable with the plurality of first felted foam strips of the first side and the plurality of second felted foam strips of the second side.

2. The dressing of claim 1, comprising a felted foam pad positioned near the central region, the plurality of first felted foam strips extending from the felted foam pad.

3. The dressing of claim 2, comprising a connection assembly coupled to the first barrier film layer at the felted foam pad, the connection assembly configured to provide airflow between the felted foam pad and a tube coupled to the connection assembly.

4. The dressing of claim 2, wherein the plurality of first felted foam strips are configured to allow airflow between each of the plurality of peninsular projections and the felted foam pad.

5. The dressing of claim 4, wherein:
the first barrier film layer and the first wound contact layer are configured to form wrinkles therein when air is removed from the dressing via the felted foam strips; and
the wrinkles allow fluid to flow therethrough.

6. The dressing of claim 1, wherein the first wound contact layer and the first barrier film layer are configured to allow visual observation of a wound through the first wound contact layer and the first barrier film layer.

7. The dressing of claim 1, wherein:
the first barrier film layer is welded to the first wound contact layer around a perimeter of the first barrier film layer and at a plurality of spot welds distributed amongst the plurality of first felted foam strips; and
the plurality of spot welds constrain movement of the plurality of first felted foam strips relative to the first barrier film layer and the first wound contact layer.

8. The dressing of claim 1, wherein the glove assembly is configured to receive a hand of a patient between the first wound contact layer and the second wound contact layer.

9. The dressing of claim 8, comprising an adhesive configured to seal the first side and the second side to a wrist of the patient when the glove assembly receives the hand;
wherein the first barrier film layer and the second barrier film layer provide a substantially airtight volume therebetween when the adhesive is sealed to the wrist of the patient.

10. A dressing, comprising:
a first side of a glove assembly including:
a first barrier film layer;
a first wound contact layer coupled to the first barrier film layer; and
a plurality of first felted foam strips positioned between the first barrier film layer and the first wound contact layer, each strip providing a manifolding pathway;
wherein the first barrier film layer and the first wound contact layer comprise a central region and a plurality of peninsular projections extending therefrom in a shape of a hand, and
wherein each strip of the plurality of first felted foam strips extends from the central region to one of the plurality of peninsular projections,
a second side of the glove assembly coupled to the first side of the glove assembly, the second side of the glove assembly including:
a second barrier film layer;
a second wound contact layer coupled to the second barrier film layer; and
a plurality of second felted foam strips positioned between the second barrier film layer and the second wound contact layer, each strip providing a manifolding pathway;
an adhesive configured to seal the first side and the second side to a wrist of a patient when the glove assembly receives a hand of the patient;
wherein the first barrier film layer and the second barrier film layer provide a substantially airtight volume therebetween when the adhesive is sealed to the wrist of the patient.

* * * * *